United States Patent
James

(10) Patent No.: US 8,376,984 B2
(45) Date of Patent: Feb. 19, 2013

(54) APPARATUS, SYSTEM, AND METHOD TO DELIVER OPTIMAL ELEMENTS IN ORDER TO ENHANCE THE AESTHETIC APPEARANCE OF THE SKIN

(75) Inventor: Terry L. James, Fairview, TX (US)

(73) Assignee: Terry L. James, Fairview, TX (US)

( * ) Notice: Subject to any disclaimer, the term of this patent is extended or adjusted under 35 U.S.C. 154(b) by 1909 days.

(21) Appl. No.: 11/183,000

(22) Filed: Jul. 14, 2005

(65) Prior Publication Data

US 2007/0073217 A1 Mar. 29, 2007

(51) Int. Cl.
*A61B 17/20* (2006.01)

(52) U.S. Cl. ......................................... 604/46

(58) Field of Classification Search .................. 606/167, 606/180, 186, 189; 604/46–48, 27, 506, 604/117
See application file for complete search history.

(56) References Cited

U.S. PATENT DOCUMENTS

| | | | | |
|---|---|---|---|---|
| 5,108,989 | A * | 4/1992 | Amento et al. | 514/12 |
| 5,436,228 | A * | 7/1995 | Postlethwaite et al. | 514/12 |
| 5,611,806 | A * | 3/1997 | Jang | 606/167 |
| 5,785,978 | A | 7/1998 | Porter et al. | 424/401 |
| 5,964,729 | A | 10/1999 | Choi et al. | 604/47 |
| 6,030,404 | A | 2/2000 | Lawson et al. | 606/186 |
| 2002/0045859 | A1 * | 4/2002 | Gartstein et al. | 604/117 |
| 2002/0099356 | A1 | 7/2002 | Unger et al. | 604/501 |
| 2003/0199811 | A1 * | 10/2003 | Sage et al. | 604/46 |
| 2004/0049251 | A1 | 3/2004 | Knowlton | 607/101 |
| 2004/0052750 | A1 * | 3/2004 | Lee et al. | 424/70.14 |
| 2004/0087992 | A1 * | 5/2004 | Gartstein et al. | 606/186 |
| 2004/0260210 | A1 | 12/2004 | Ella et al. | 601/7 |
| 2005/0137531 | A1 * | 6/2005 | Prausnitz et al. | 604/173 |

FOREIGN PATENT DOCUMENTS

DE 195 18 932 A1 5/1995

OTHER PUBLICATIONS

Horst Liebl, Co., "Confidential—Evaluation II—On the Needling-device Medical Roll-CIT," made by Environ, 5 pgs.
K.Anastassakis, M.D., Ph.D., "The Dermaroller Series," 25 pgs.
D.R. Owen, Ph.D., "Peptides, Oligopeptides, Lipopeptides and Polypeptides," Official Publication of the Society of Plastic Surgical Skin Care Specialists, 2 pgs, Spring 2005.
"History of the Dermaroller," 8 pgs.
DermaRoller™, http://www.dermaroller.de/derma_engl.htm, 4 pgs, Jul. 11, 2005.
"The Dermaroller—A New and Highly Effective Procedure to Treat Acne-Scars by Micro-Needling," 3 pgs.

(Continued)

*Primary Examiner* — Kevin C Sirmons
*Assistant Examiner* — Michael J Anderson
(74) *Attorney, Agent, or Firm* — Patent Capital Group

(57) ABSTRACT

An apparatus for delivering a bioactive material to a subterranean layer of a skin architecture is provided that includes a head including one or more needles that are operable to penetrate a stratum corneum of a skin. A bioactive material is disposed on one or more of the needles, whereby movement of the head operates to pick up the bioactive material and to deliver a portion of the bioactive material to a selected location, the selected location being a dermis, or an epidermis, or both the dermis and the epidermis. In more particular embodiments, the bioactive material is a macromolecule substance that is part of a group of substances, the group consisting of a protein, a vitamin, a gene, a growth agent, a drug, and a peptide. The needles create an injury that triggers collagen production from one or more fibroblasts in the skin.

25 Claims, 4 Drawing Sheets

OTHER PUBLICATIONS

Horst Liebl, Co., "The Collagen-Induction-Therapy CIT with the CIT-Roller," 3 pgs.

DermaRoller™-MODELS, 3 pgs, Mar. 2005.

"The Dermaroller—An effective alternative for scar-therapies," 5 pgs, Mar. 2005.

"The Collagen-Induction-Therapy (CIT) with the DermaRoller™—The "soft" alternative for all common Laser & Peeling-Methods," 5 pgs, Dec. 2003.

"Frequently Asked Questions (FAQs) About the DermaRoller™," 4 pgs, Mar. 2005.

Horst Liebl, Co., "Technical evaluation of the ROLL-CIT," Manufactured by ENVIRON—South Africa, 3 pgs, Dec. 2005.

Horst Liebl, Co., "Technical Data & Description of the DermaRoller™," 1 pg, Dec. 1, 2002.

Clark, R. A., "Biology of Dermal Wound Repair", Dermatologic Clinics, Oct. 1993, vol. 11, No. 4, pp. 647-666, Oct. 1993.

* cited by examiner

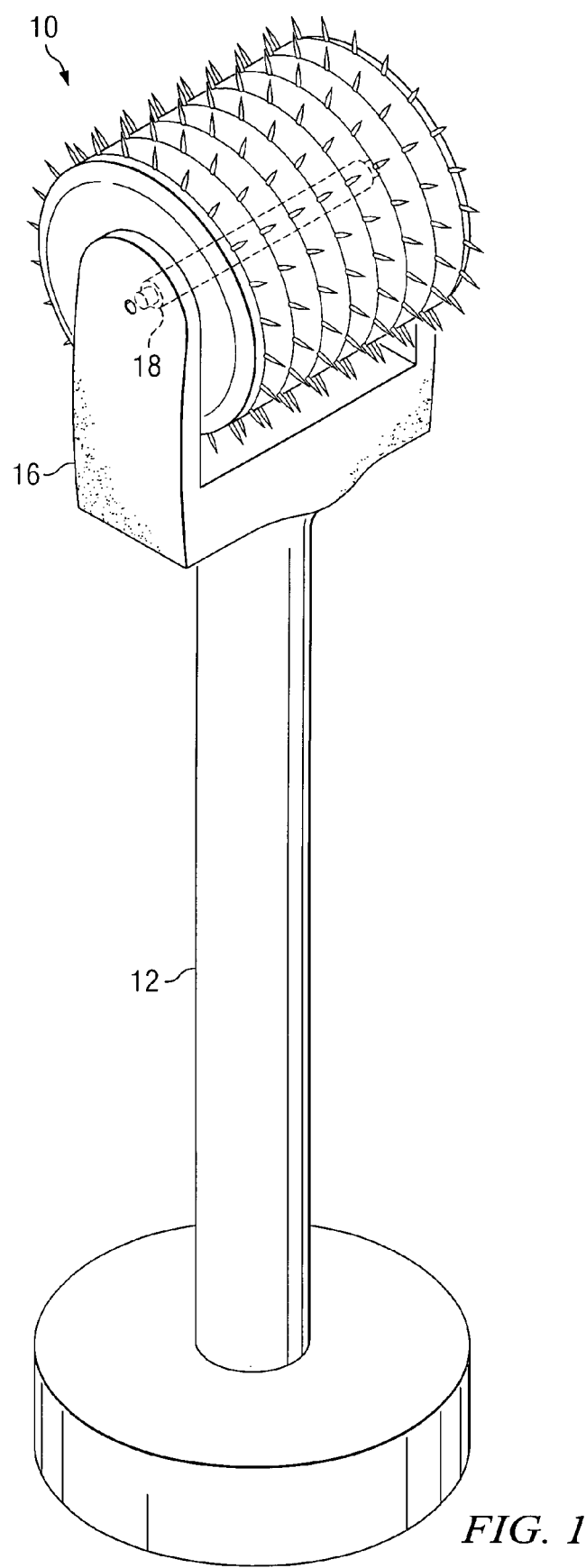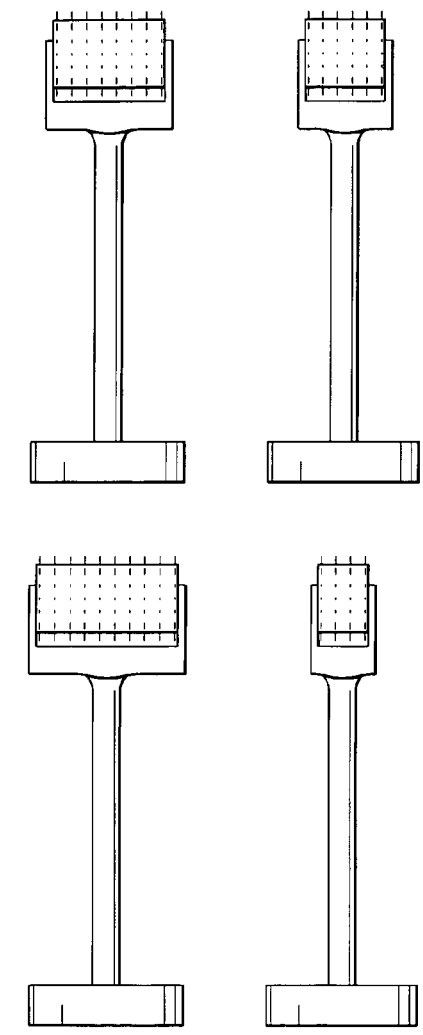
FIG. 1
FIG. 2

APPARATUS, SYSTEM, AND METHOD TO DELIVER OPTIMAL ELEMENTS IN ORDER TO ENHANCE THE AESTHETIC APPEARANCE OF THE SKIN

TECHNICAL FIELD OF THE INVENTION

This invention relates in general to a skin treatment protocol and, more particularly, to an apparatus, a system, and a method to deliver optimal elements in order to enhance the aesthetic appearance of the skin.

BACKGROUND OF THE INVENTION

Skin is a complex composite of several layered tissues that function cooperatively. The skin is the largest organ of the human body and forms a barrier between the physical body and the outside environment. This barrier remains open and permeable to the environment, which allows for an exchange of heat, air, and fluids. The skin consists of three layers, namely: the epidermis, the dermis, and the subcutaneous layer.

The epidermis is the outer layer that covers the whole outside of the body. The epidermis contains numerous nerve endings that make the skin into one large sense organ that is operable to detect heat, cold, light, and touch. The outer layer of the epidermis, called the stratum corneum, is constantly being shed and, subsequently, replaced with new layers from below the epidermis. In the context of skin treatments, the stratum corneum operates as the rate-limiting barrier to percutaneous absorption and, further, fulfills one of its objectives by serving as a protective barrier. The stratum corneum is composed of dense layers of dead flattened cells. The stratum corneum is filled with fibrous protein keratin that is derived from the epidermis beneath. In its absence, for example when the skin is partially removed by some disease process, the absorption of drugs across the skin is increased.

The three layers of skin cooperate in a precise manner in order to produce an individual's outward appearance. Virtually all human beings are fixated on their appearance, albeit at varying degrees of interest. As can be appreciated, a person's age or health can be readily inferred from their skin. In other cases, the skin can signify previous acne issues, scarring (of any type), or other dermatological abnormalities that compromise a person's physical attractiveness.

Currently, there are thousands of treatment schemes, practices, and protocols that, ironically enough, are all claimed by their supporters to reverse the aging process and/or produce unblemished skin. Unfortunately, only minor fractions of the active substances in virtually all creams, gels, or lotions can penetrate the surface of the skin. The majority of the marketed products are simply wiped or washed off the face. Hence, the active ingredients of most cosmetic creams, how ever potent and wonderful, never really penetrate deeply enough into the skin to be effective. Note that the poor penetration characteristic of a given face cream is a natural and an expected physiological reaction of the skin.

Today, it is uniformly accepted that in order to achieve acceptable transdermal concentration of substances, the stratum corneum barrier must be breached or traversed. In order to increase skin permeability, a number of different approaches have been developed: ranging from chemical/lipid enhancers to electric fields employing iontophoresis and electroporation to pressure waves generated by ultrasound or photoacoustic effects. With the exception of chemical/lipid enhancers, all of these methods share the common goal of attempting to disrupt the stratum corneum structure in order to create holes big enough for molecules to pass through the stratum corneum.

The human skin represents an attractive alternative method for the delivery of drug administration because it can provide a patient-friendly interface for systemic drug administration, an avoidance of first-pass metabolism, and a sustained and controlled delivery of a substance. Previously, the only means of delivering molecules through the skin was by either hypodermic needles or transdermal patches.

Hypodermic injection techniques are demanding for the doctor and problematic for the patient, as they cause local pain and trauma. Hypodermic needles effectively deliver any drug at virtually any rate across the skin, but are limited by pain, the need for medical expertise (which increases cost), and the difficulty of having controlled delivery over long periods of time.

In contrast, transdermal patches largely eliminate many of these limitations, but suffer from an inability to deliver most drugs across skin at useful rates. Until today, the only drugs that have been marketed in a patch-delivery method are scopolamine, nitroglycerine, nicotine, clonidine, fentanyl, estradiol, testosterone, lidocaine, and oxybutinin. The reason why these drugs have been successfully delivered in a patch form is that their small molecular size (e.g. smaller than 500 Daltons) allows for a limited passive diffusion through the stratum corneum.

In summation, the disadvantages of existing skin treatment systems and devices in the market place are noticeable. The problem with simply applying any cosmetic material on the skin is that the stratum corneum is impregnable or impermeable. Elements simply do not go through this barrier, which is why most current cosmetic products are inactive, as they only linger on the surface of the skin and fail to reach the point where they could actually be beneficial. Hence, the challenge is not only to find an optimal material to be delivered to the certain layers of the skin (e.g. the dermis), but how to get the chemical agent to the point where it is most effective. This represents a classic pharmacological problem. Concisely stated, the objective is to find the right agent (having the right concentration) and to employ the right delivery system in order to reach the right target cell location. Details concerning each of these objectives are discussed more fully below in the context of the present invention.

SUMMARY OF THE INVENTION

From the foregoing, it may be appreciated by those skilled in the art that a need has arisen for an improved apparatus, system, and method for achieving superior skin treatments. In accordance with an embodiment of the present invention, an apparatus, a system, and a method for triggering a reaction from a target cell in the dermis or the epidermis are provided that substantially eliminate or greatly reduce disadvantages and problems associated with conventional skin care approaches and instruments.

An apparatus for delivering a bioactive material to a subterranean layer of a skin architecture is provided that includes a head including one or more needles that are operable to penetrate a stratum corneum of a skin. A bioactive material is disposed on one or more of the needles, whereby movement of the head operates to pick up the bioactive material and to deliver a portion of the bioactive material to a selected location, the selected location being a dermis, or an epidermis, or both the dermis and the epidermis. In more particular embodiments, the bioactive material is a macromolecule substance that is part of a group of substances, the group consisting of a protein, a vitamin, a gene, a growth agent, a drug, and a peptide. In addition, the needles create an injury that triggers collagen production from one or more fibroblasts in the skin.

Certain embodiments of the present invention may provide a number of technical advantages. For example, according to one embodiment of the present invention, an apparatus and a method are provided that achieve an extremely high absorption rate for any type of chemical substance. This is due to the hole-creation mechanism of the head of the present invention. Providing holes in a given surface can increase the permeability of the surface, but this passive transfusion only offers one aspect of the present invention. A second aspect of the present invention addresses how to optimally transport a bioactive material to the portions of the skin that can best utilize the material. Even in the presence of holes in the surface of the skin, reliance on the actual molecules to "deliver themselves" is tenuous.

The present invention operates to account for this important concept, as the needles actually gather or harvest the surface-layer materials (i.e. bioactive materials) and force them into their targeted zone. The needles pick up or collect the materials on the surface at the targeted site and re-deposit these materials to the precise location where they are needed the most. This physical transport, from needle tip to the subterranean dermis, stands in contrast to a rudimentary chemical diffusion that cannot offer the benefits realized by the present invention. Thus, the movement of a substance from the surface of the epidermis to the dermis that is provided by the present invention overcomes the inadequacies of simply painting the top of the epidermis with chemicals, how ever effective the chemical may be, without actually accounting for how the chemicals will travel to the appropriate location. Thus, the present invention can offer optimal collagen induction by delivering a critical concentration of a bioactive substance to targeted cells in the dermis, which produces collagen.

Moreover, the device of the present invention can provide for the softening of scars and the realignment of old collagen bundles, while preserving the epidermis during the skin treatment procedure. In contrast to other inferior skin treatment protocols, the design and operation of the present invention yields no permanent damage to the skin and is relatively pain free. Also, because of the needle arrangement, there is little possibility for bleeding, infection, discoloration, or other dermatological complications on the treated area. It should also be noted that other skin treatment systems generally require a significant recovery time, such as laser treatments, for example. The present invention provides a minimal state of convalescence: only about 24-48 hours in actual healing time is necessary. Other advantages are described below.

Certain embodiments of the present invention may enjoy some, all, or none of these advantages. Other technical advantages may be readily apparent to one skilled in the art from the following figures, description, and claims.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which:

FIG. 1 is a simplified block diagram illustrating an apparatus for delivering optimal elements to enhance the aesthetic appearance of the skin in accordance with one embodiment of the present invention;

FIG. 2 is a schematic view of several example sizes of the rolling device of FIG. 1;

DETAILED DESCRIPTION OF EXAMPLE EMBODIMENTS

Figure 3:
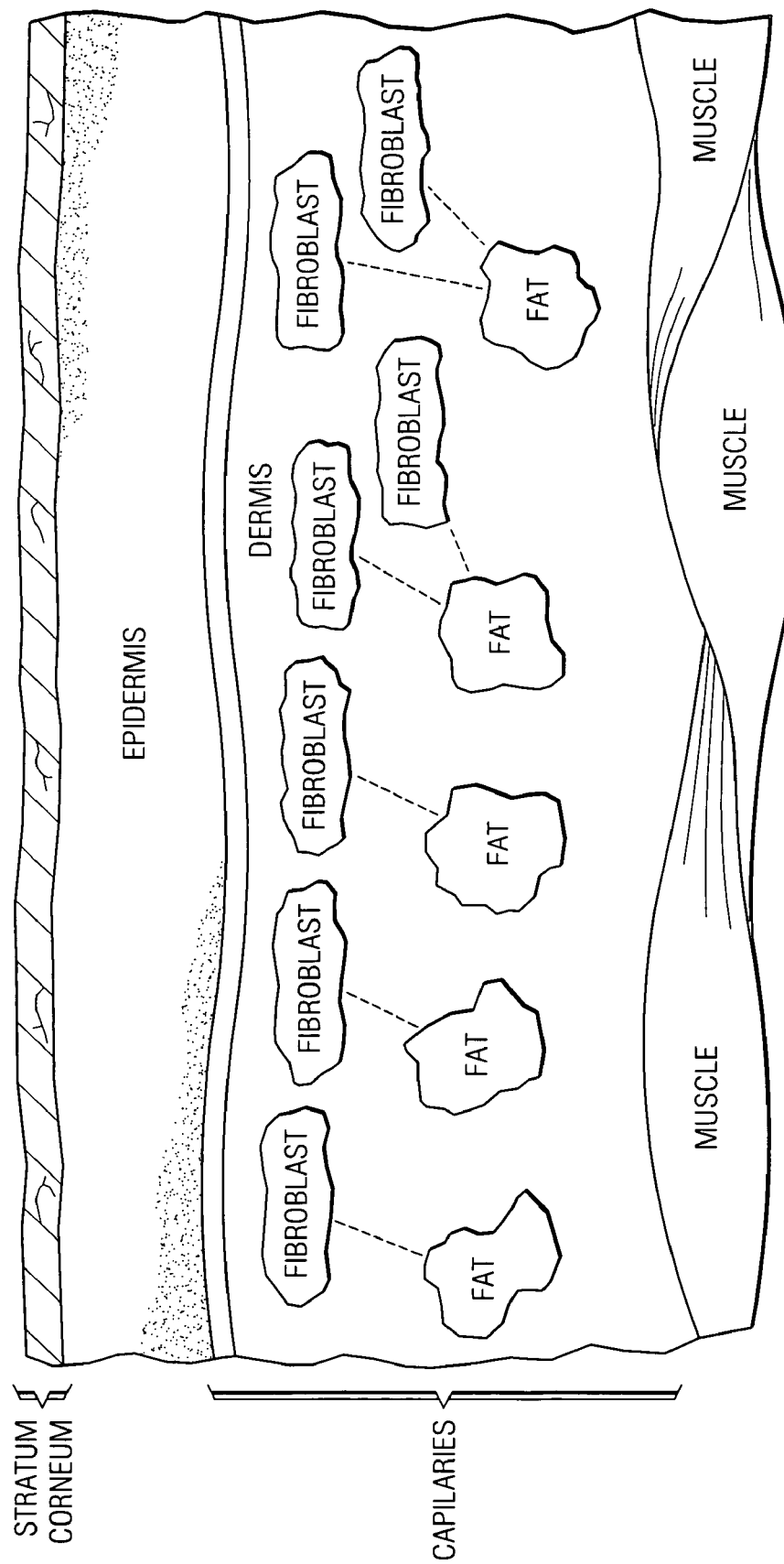
FIG. 3 is a simplified block diagram of an example skin architecture, which may be generally prevalent in a given patient.

FIG. 1 is a simplified block diagram illustrating a rolling device 10 for delivering optimal elements to enhance the aesthetic appearance of the skin in accordance with one embodiment of the present invention. Rolling device 10 includes a fork element 12, which includes a handle. Rolling device 10 also includes a head 16, which includes a number of needles. In addition, rolling device 10 includes a pin 18, which operates to secure head 16 to fork element 12.

Rolling device 10 offers a mechanism for the infiltration of active substances through the epidermal barrier. Note that the infiltration of substances (cosmetics or drugs) through the stratum corneum is the classic objective for many scientists relegated with the task of addressing how to enhance the aesthetic appearance of an individual's skin. Many attempts were made in the past to build a device for the direct infiltration of substances through the outer skin layers without destroying the epidermis or the dermis. All attempts to achieve that goal have been inadequate due to poor tooling, improper material being delivered to incorrect locations of the skin, and ill-conceived needle patterning and/or needle length.

These deficiencies, and others, are overcome by the present invention. Rolling device 10 has a number of advantages over other instruments, including its unique design, its needle pattern or its exact needle placement, its needle length, and the unique material that is to be delivered to the epidermis or the dermis. All of these aspects of the present invention are detailed herein, and explained more fully with reference to subsequent FIGURES.

Microneedles, which represent the cornerstone of the present invention, sit at the interface between transdermal patches and hypodermic needles, attempting to gain the advantages of both and eliminate the disadvantages of each approach. Microneedles may be small enough to capture the convenience of patches, but large enough to create micrometer-scale pathways across the skin for drug delivery of even the largest macromolecules. Microneedles can be painlessly inserted into the skin of human subjects and their use does not require accompanying medical expertise. Rolling device 10 shares the advantages of the typical microneedle array, but also has a unique way of mechanically driving the applied substance under the skin, through the holes already created by needles of rolling device 10. The needles on the surface of rolling device create miniscule holes (e.g. of 0.02 mm diameter and 0.18 mm in depth), while the cylinder itself literally pushes (mechanically) the applied substance inside the holes and deposits the substance under the skin. It should be noted that all macro-molecular delivery system procedures should account of patient sensitivity. Hence, rolling device 10 can be used in conjunction with a topical anesthetic or a local anesthetic where appropriate.

As highlighted above, in order to realize the benefit from any cosmetic substance and their corresponding ingredients, the epidermal barrier must be overcome or semi-penetrated. This would enhance the delivery of active substances into the deeper skin layers. Many factors govern the rate at which drugs and cosmetics penetrate the skin. These factors can include the size of the molecule, the lipophilicity of the molecule, the type of formulation, the presence of penetration enhances, and the physical state of the stratum corneum. The rate of percutaneous penetration can also vary according to the anatomic site under consideration.

From a physical aspect, there is considerable malleability in the design and architecture of rolling device 10. The following design parameters delineate the specifications for a given example embodiment, but are completely non-limiting. The specifications proffered herein in this document can be departed from, while such resulting products are clearly within the scope of the present invention. The design specifications herein have only been offered for purposes of teaching and discussion and, thus, should not be construed in any way to limit the broad applications and configurations provided by the tendered invention.

Rolling device 10 is generally a drum-shaped device (roller head) that is attached to a handle that can be manipulated by a patient autonomously, or than can be operated by a practicing physician where appropriate. In order to achieve a maximum number of pricks per square-unit (inch or cm), the following parameters can be followed: 1) the diameter of the roller head can be about 5-30 mm; 2) the needles of rolling device 10 are suitably arranged (e.g. in a 12-25° angle range [or less or more in some cases, some of these parameters being confined by manufacturing constraints]); and 3) in order to optimize delivery, 6-14 needle rows are employed.

With respect to handle 12, it should be somewhat flexible, of a reasonable weight, and capable of facilitating an easy operation of rolling device 10. In order to optimally deliver the active substance into the desired skin depth, various needle lengths can be used (e.g. from 0.15 mm to 2.0 mm or greater where needed). The needle lengths can control the depth levels and, thus, the exact location of where the bioactive material will be delivered. The needles themselves are specifically designed of a hard steel (e.g. steel quality close to type 1.4305) and are sharp enough to penetrate the surface of the skin with minimal effort. Concerning the roller head, it can consist of multiple plastic chips. Several inner chips could include the following dimensions: 2.5 mm thick and 20 mm in diameter. Each chip may include 24 needle beds (e.g. 0.3 mm deep). The head also includes two outer discs, one with needle beds and one without. In one example, the thickness of each is 2 mm.

Rolling device 10 has a somewhat larger needle diameter (as compared to other micro-needling systems), larger needle length, and larger interneedle spacing than other microfibricated arrays. In one embodiment, rolling device 10 has needles of 130 µm length and rolling the device 15 times over the same area will result in >250 pricks/cm². Needles can be manufactured from stainless steel, and the microneedle fracture force is hundreds of times greater than the skin insertion force. The size of the needles is sufficient to overcome natural skin dermatoglyphics and still pierce the stratum corneum of even the areas with the thickest epidermis.

It should be noted that there is a general lack of pain caused by the needles of the present invention. Microneedles are of interest primarily because they offer the promise of a painless drug delivery. Because the skin's stratum corneum barrier has no innervation, skin anatomy provides the opportunity to pierce needles across the stratum corneum without stimulating nerves. In actual current practice, there is no evidence of microneedles penetrating just 10-20 µm across stratum corneum without entering the viable epidermis, where nerves are found. Instead, microneedles are inserted at least into the epidermis. Nevertheless, microneedles are still reported as painless, probably because their small size reduces the odds of encountering a nerve or stimulating it to produce a painful sensation.

The present invention has a host of potential applications. For example percutaneous collagen induction therapy is an important area that could benefit greatly from the teachings of the present invention. Percutaneous collagen induction is the process of initiating the physiological collagen production of the dermis without causing permanent damage to the epidermal layer of the skin. The best way to achieve this is by moving rolling device 10 multiple times, back-and-forth in a star-like fashion over the whole skin area to be treated. Thousands of miniscule wounds are caused by this operation. At the same time, channels are opened in the stratum corneum. The physiological reaction of the dermis to this miniscule (yet substantial) injury is collagen production. The combination of controlled trauma to the dermis and the supply of external bioactive agents cause an optimal natural collagen production.

Hence, rolling of rolling device 10 over the skin will cause hundreds of wounds, while creating tiny holes on the epidermis, which will close in hours. This operation will start an aseptic inflammation process, which will result in collagen production. In one context, rolling of rolling device 10 over scar tissue is an ideal procedure with a vertical subcision because the rolling of the needles over the scar will vertically cut the fibrous septae and release the skin of its fisbromuscular attachment to deeper tissues. Rolling device 10 can also specifically help release tension coming from the under lying superficial musculoaponeurotic system (SMAS) in facial areas, which is the main mechanism by which facial wrinkles are formed.

Each tiny wound created by rolling device 10 goes through the three classic phases of wound healing: 1) inflammation; 2) proliferation; and 3) tissue remodeling. The needle only penetrates through the epidermis and does not remove it. Therefore, the epidermis is only pierced and rapidly heals in a matter of hours because keratinocytes are highly elastic and flexible. This injury does cause some localized damage and micro-bleeding, but this is not visible on the skin.

The needle pricks of rolling device 10 can penetrate to their full length into the dermis and trigger the inflammation phase. Skin capillaries are ruptured and so blood cells and serum get into the surrounding tissue. A complex chemical cascade determines the formation of hundreds of miniscule clots, the vascular permeability, the chamoattraction for leucocytes, and the recruitment of fibroblasts in the wounded area. Platelets cause clotting and release chemotactic factors like platelet derived growth factor (PDGF), transforming growth factor (TGF), and fibroblast growth factor (FGF) that initiate an invasion of other platelets, leucocytes, and fibroblasts.

Neutrophils act on the damaged tissue by removing the debris of the damaged collagen and microclots. This reaction is automatic and produces a surge of activity that inevitably leads to the fibroblast being instructed to produce more collagen and more elastin. The stimulation of the fibroblast is one important objective of the present invention. The re-epithelialisation occurs within a few hours after needling and is more due to keratinocyte migration rather than proliferation. When the keratinocytes have joined together, they start producing the components to re-establish the basement membrane with laminin and collagen types IV and VII. Days after the injury, the keratinocytes start proliferating and thicken the epidermis.

Fibroblasts migrate into the wound and produce collagen, proteoglycans, elastin, and other matrix proteins. Initially, after needle damage, the disruption of the blood vessels causes a moderate amount of hypoxia. The low oxygen tension stimulates the fibroblast to produce more TGF, PDGF, and vascular endothelial factor (VEGF). Prevascularisation occurs quite soon after needling. TGF is a powerful chemotactic agent for fibroblasts, which migrate into the wound about 48 hours after injury and which start producing collagen I and III and elastin. Collagen type III is the dominant form of collagen in the early-wound healing phase and becomes the greatest at 5-7 days after injury. The collagen is laid down on the upper dermis just below the basal layer of the epidermis.

Tissue remodeling continues for months after the injury and is mainly overtaken by the fibroblasts. By day 5 after the skin treatment session associated with rolling device 10, the fibronectin matrix is formed along the axis in which fibroblasts are aligned. This is the same axis where collagen will also be formed. TGF and other growth factors can play an important part in the formation of this matrix.

Over a period of 6-12 months, collagen type III is gradually replaced by collagen type I. This type of collagen gives increased tensile strength to the skin. Metalloproteinases are essential for this conversion process. Collagen slowly shortens after a few months and so the tightening of the skin is progressive over the next few months. The results can mimic those obtained with a laser, but without destroying the epidermis.

FIG. 2 is a schematic view of several example sizes of rolling device 10 of FIG. 1. Each of the rolling device examples includes a stand, which represents a simply base that may be used to store or to stabilize the rolling device. The roller head models may have a width of 20 mm and have 192 needles with different lengths as requested or needed by a given patient. A smaller model could include a 10 mm width, providing 96 needles with different lengths. Other ranges and sizes could easily be manufactured and be based on particular needs. The needles can be used repeatedly on human skin numerous times (e.g. 200 times or more) without loosing their sharpness. The sharpness of the needles should yield a piercing of the stratum corneum with minimal effort. The handle may be constructed from an ABS plastic, whereby the roller head is attached to the upper handle fork by a stainless steel axis. Fork element 12 is designed in such a way that the two brackets that hold the axis are under tension. The inner width is about 20.5 mm in one example. The axis has a width of about 22 mm and spreads the two brackets apart.

Again, it is imperative to note that the description presented above is only an example of some embodiments of the present inventions. The components of FIG. 1 and FIG. 2 may be assembled in any fashion in order to achieve the teachings of the present invention. In addition, rolling device 10 may be manufactured as an integral piece, whereby dismantling of the device is impossible. Additionally, the rolling head or handle may be changed considerably: such changes being based on specific arrangements or particular patient needs.

FIG. 3 is a simplified block diagram of an example skin architecture, which may be generally prevalent in a given patient. FIG. 3 includes a stratum corneum layer (which represents the surface of the skin), an epidermis, and a dermis section. A muscle segment and a fat segment are also present in the skin architecture, as is shown. A capillaries section is also identified in FIG. 3. The significant component of FIG. 3 is the fibroblast, which is thoroughly discussed below.

The epidermis of FIG. 3 is purely a cellular structure without blood vessels or nerves. The different layers of the epidermis include the stratum corneum, stratum granulosum, stratum malpighii (prickle cell layer), stratum spinosum, (ret mucosum) and the basal layer (stratum germinativum). It is simple to draw diagrams of skin that delineate the epidermis and dermis, the two distinctly different layers of skin. In realty however, each layer is highly dependent on the other layer to effectively perform its own function. Anything that affects the epidermis will also have an effect on the dermis as a subsequent reaction. Anything that affects the dermis usually will affect the function of the epidermis. Obviously, most things that affect the dermis without mechanically affecting the epidermis from the outside will be from internal origin, such as a disease process, a blood flow related problem, or other abnormal circumstances. An exception to this is the effect of the UVA spectrum of ultraviolet radiation. UVA passes from the external through the epidermis and dissipates its energy within the dermal structure. UVB is completely absorbed within the epidermis. UVA damage occurs primarily in the dermis. It is visualized as the signs of aging related to damaged collagen and elastin fiber. UVB damage manifests itself as both pre-cancerous skin lesions (actinic keratoses), rough texture to skin, uneven pigment (melasma), and epidermal skin cancers (including melanoma).

The epidermis comprises the external layer of the skin and functions as a mechanical barrier to the outside environment. As a barrier, it helps the retention of fluid within the body to prevent the entire organism from evaporation and death. The unique network of epidermal cells (with their intercellular connections) allows moisture to pass through the external surface of the skin in both directions. This allows consistency for pliability and softness, which are essential for stretching or bending of joints.

The cells of the dermis include fibroblasts, which form the fibrous tissue and the matrix (ground substance) for the skin. The functions of fibroblasts include: production of collagen and elastic tissue, synthesizing of mucopolysaccharides, and metabolism of cholesterol and steroids. Hence, the dermis is composed mainly of collagen fibers, which are synthesized by fibroblast. The thickness of collagen depends on different factors such as age, sex, and body sites. The collagen layer is organized into a smooth superficial layer under the epidermis at the level of papillae and is coarse in the deeper layers. The collagen fibers give the skin its toughness and elasticity. Elastin fibers are associated with the collagen fibers and both are surrounded by mucopolysaccharides.

In the context of topical drug delivery across these layers of the skin, it should be recognized that to be effective, drugs must reach an intended site in the body, at an effective concentration, and for an appropriate length of time. Currently, the vast majority of effective drugs are administered either orally or by injection. However, there are numerous drugs for which these modes of administration are not well-suited. For example, oral administration of certain drugs may result in irritation of the gastro-intestinal tract or undesirable rapid first pass metabolism in the liver and gastro-intestinal tract. First pass metabolism, which refers to the chemical breakdown of compounds, can result in a significant reduction in the amount of a drug reaching its intended site of activity in the body. In some cases, liver damage may occur due to the toxicities associated with the breakdown of a particular drug by the liver. In the case of injectable drugs, administration may be painful and in many cases requires frequent and costly office visits to treat chronic conditions.

When oral administration of drugs is not feasible due to poor drug absorption or enzymatic degradation in the gastrointestinal tract or liver, injection using a painful hypodermic needle is the most common alternative. The development of more sophisticated drugs has demanded the need for more sophisticated methods to deliver those drugs. Conventional drug delivery techniques using pills and injections are often not suitable for new protein-based, DNA based, and other therapeutic compounds produced by modem biotechnology.

An approach that is more appealing to patients, and offers the possibility of controlled release over time, is drug delivery across the skin. This approach avoids degradation in the gastrointestinal tract and first-pass effects of the liver associated with oral delivery as well as the pain and inconvenience of intravenous or intramuscular injection. Moreover, it offers the possibility to continuously control the delivery rate in contrast to conventional methods that deliver a large, discrete bolus of the drug. However, transdermal delivery is severely limited by the inability of the large majority of drugs to cross skin at therapeutic rates due to the great barrier imposed by skin's outer stratum corneum layer.

Hence, delivering drug molecules through the skin is incredibly challenging. The skin naturally serves as the primary barrier that prevents outside organisms, chemicals, and toxins from easily entering the body. As outlined above, human skin is made up of three layers: 1) the outer layer, the stratum corneum; 2) the middle layer, the viable epidermis; and 3) the inner layer, the dermis.

The stratum corneum acts as the main barrier to drug delivery. Delivery of a drug through the stratum corneum depends both on the type of topical drug delivery technology used and on the drug's physical and chemical characteristics (including molecular size and shape, its solubility in lipids and water, and its melting point). Certain chemicals can increase the permeability of the stratum corneum, thereby temporarily allowing for enhanced penetration of pharmaceuticals into the skin or through the skin and into the body. Strong organic solvents are one type of chemical penetration enhancer. These solvents work by dissolving and extracting lipids from the stratum corneum, leaving gaps in the lipid matrix through which drug molecules can then pass. One of the main side effects of strong organic solvents, however, is a relatively high level of skin irritation in the area of application.

For purposes of skin rejuvenation, the key cells in many skin treatment protocols are the fibroblast, which produce collagen. Collagen can be thought of as the steel beams in a building: providing structure and volume. There is a companion to collagen in this region, namely elastin, which (as its name suggests) provides elasticity for the skin. In general, the dermis is made up of about 95% collagen and 5% elastin.

Over time, collagen-turnover reduces. For example, a child's skin is vibrant because there is a plethora of collagen fiber turnover occurring in the dermis. A typical collagen-turnover for a child (10-12 years of age) could be every 30 days. In contrast, a person who is 85 years old may only be experiencing a collagen turnover every 12 months. Turnover and total collagen volume are the two biggest factors in wrinkle production. From one perspective, aging can simply be thought of as a collagen deficit.

There are generally three types of wrinkles: 1) epidermis/dermis separation wrinkling (generally produced through ultra-violet rays); 2) mechanical wrinkling; and 3) dermal wrinkling, which corresponds to a complete loss of collagen in the dermis (generally occurring during the later years of an individual's life). With regard to the mechanical aspect of wrinkling, there are fibers that attach the muscle to the dermis. This causes the facial expression movements as the muscle contracts (e.g. wrinkling your forehead, laughing, raising your eyebrows, etc.). When a person is botoxed, the muscle is inhibited from movement and remains rigid (or simply stays in one position). Because a young person's collagen supply and quality is so high, their skin can easily withstand any mechanical stresses on the skin. However, as a person ages, the resiliency of the collagen decreases and the supply demand aspect of collagen begins to deteriorate. This is where furrowing or wrinkling can begin.

The fundamental principle behind the skin rejuvenation efforts of the present invention is injury. This appears to be paradoxical, but, in fact, is exactly the approach taken by most that operate in the field of skin revitalizing. Procedures such as laser treatments (soft lasers, CO2 lasers, etc.), chemical peels, and micro-derm abrasion all create injuries. Note that when a man shaves his face, even this provides a beneficial mild injury to the stratum corneum. A simple daily shaving (which scrapes the stratum corneum) is thought to be one reason why men appear to age more slowly than women. Thus, there is a continuum of treatments related to the critical issue of injury. Note that if an injury exceeds a 50% damage level to the dermis, then the architecture of the skin is comprised (perhaps permanently, which would produce scarring). Hence, almost half of the dermis can be removed and it will duplicate, rejuvenate, and reconstitute itself successfully. Many treatments (e.g. skin lasers) are intended to minimize injury to the epidermis and deliver a specific injury to the dermis. Hence, the objective is a selected tissue injury, while minimizing inflammatory responses, which increases the likelihood of hyper-pigmentation, scarring, and decreasing the desired rejuvenation effect.

Figure 4:
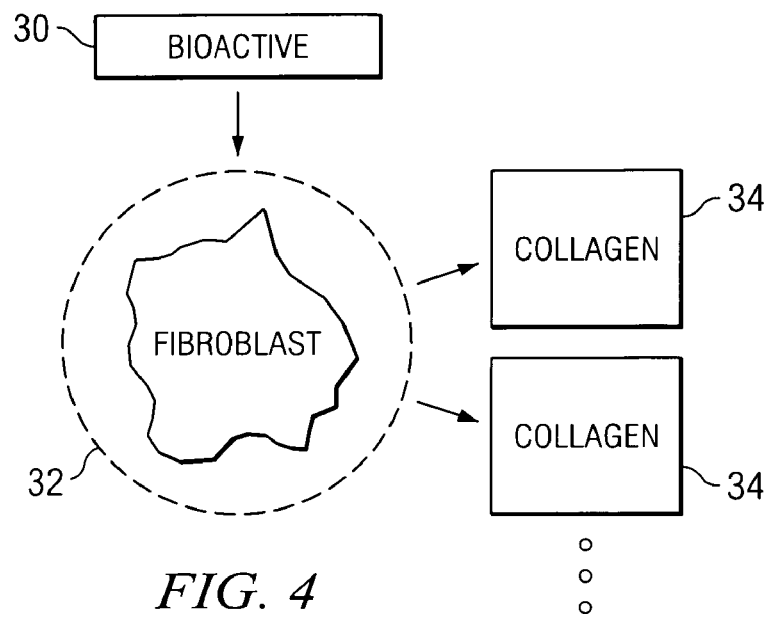
FIG. 4 is a simplified block diagram of an interaction involving a fibroblast in accordance with one embodiment of the present invention.

With this background in place and understood, the audience is directed specifically to the fibroblast, which represents an invaluable component in the skin treatment equation. FIG. 4 is a simplified block diagram of an interaction involving a fibroblast 32 in accordance with one embodiment of the present invention. FIG. 4 illustrates a given bioactive 30 being used on fibroblast 32, which subsequently produces the desired collagen elements 34.

Note that there are several ways to produce the appropriate response from a fibroblast (i.e. to trigger collagen production). A simple collagen production is not enough to justify many treatments. The issue is whether the procedure can produce enough collagen to achieve a noticeable cosmetic effect. One way to stimulate the fibroblast is to wound the skin. The wounding procedure initiates a cascade of events that yields peptides and growth factors. These elements would ultimately stimulate the fibroblast to produce collagen. But another way to achieve this result is to avoid the injury and simply deliver a peptide (or a growth factor, etc.) directly to a specific region of the skin. Hence, when the growth factors or peptides are delivered directly to the fibroblast, then a significant advancement is achieved by the present invention. The growth agents and the peptides are included within the term 'bioactive material' as used herein in this document. The bioactive material can cause proliferation of collagen without irritation. Bioactive materials can also include a vitamin, a protein, a gene, or any other suitable macromolecule.

The present invention can offer is a huge increase in the amount of a substance that is delivered to the targeted site. Some of this is due to a driving mechanism provided by rolling device 10. To illustrate the enhanced capabilities of the present invention, consider that case of being given a local anesthetic. The drug in such an instance is delivered via a needle, whereby the needle penetrates the skin. If that same drug were simply poured over the skin, it would not have the desired effect because the stratum corneum would serve as a barrier and would not allow the drug to reach its intended destination (i.e. below the skin where the nerves/pain fibers reside). Thus, the drug is injected directly into the dermis to achieve an optimal result. The same theory could be applied to cosmetic skin treatments, as delivering a bioactive material (as described herein) could be delivered to the dermis using a single syringe.

With this in mind, consider a rolling device (such as that provided by the present invention) that consists of multiple mini-syringes and that is capable of offering variable lengths of needles. There are three aspects to such a device: 1) the simultaneous puncturing of the dermis, the epidermis, or both by a plethora of needles present on rolling device 10 (this causes a micro-injury and allows for the production of collagen); 2) the needles effectively create a channel, whereby a given substance (e.g. growth stimulants) can leak, or be directed, through the channel; and 3) the needles physically transport a substance from the skin to the selected area (i.e. the dermis, the epidermis, or both). The latter operation may be achieved as the needles are rolled over the surface, whereby the substance is picked up by the needles and then stuffed into the newly-created holes or physically driven into the depths of the skin.

While it is true that providing holes in a given surface can increase the permeability of the surface, this passive transfusion only offers half of the idea proffered by the present invention. The second part, which is equally beneficial, deals with the importance of having a critical concentration of a substance in the actual dermis. In order to deliver that critical concentration to the dermis, holes may be provided to increase permeability in the skin, but also a physical transport of the bioactive materials from the surface layer to the dermis is necessary. This represents an invaluable tool for achieving the desired effect and, further, represents the second part of the present invention. The needles pick up or collect the materials on the surface and re-deposit these materials to the precise location where they are needed the most. This physical transport, from needle tip to the selected epidermal or dermal targeted cell, stands in contrast to a rudimentary chemical diffusion that cannot offer the benefits realized by the present invention.

Note that even in the presence of holes in the surface of the skin, reliance on the actual molecules to "deliver themselves" is tenuous. The second aspect of the present invention operates to account for this important concept, as the needles actually gather or harvest the surface-layer materials and force them into their targeted zone. Thus, the movement of a substance from the surface of the skin to the epidermis or to the dermis that is provided by the present invention overcomes the inadequacies of simply painting the skin surface with chemicals, how ever effective the chemical may be, without actually accounting for how the chemicals will travel to the appropriate location.

As can be appreciated from the discussion above, the placement and the design of the needle (including its architecture, its sharpness, its material, its diameter, its width, its length, its separation, its flexibility, and its hardness) becomes of paramount importance. In addition, its associated pattern, its positioning (on the head), and its angle is critical for selective site delivery. Also, the idea of needle placement or arrangement is essential, as it relates to the pattern or density (i.e. how many needles per square centimeter or millimeter) of the needles that are present on the head. If a simple hole were poked in the stratum corneum and a measurement were taken of how much bioactive agent passively moved from the surface to the dermis, there would be a certain percentage (e.g. 90%) of improvement in the delivery of the substance sought to be delivered at the treatment site due to passive diffusion. However, if an instrument were designed with certain needle specifications (as described previously) such that rolling the instrument would result in transporting a desired number of molecules per square centimeters, then delivery of a given bioactive substance may be more greatly enhanced (e.g. 1000%). Physical transport to targeted cells in a selected skin area (e.g. the epidermis or the dermis) is a critical aspect of the present invention because this component will yield a critical concentration of bioactive agents in target cites. Hence, effective physical transport begets delivery of a critical concentration to a selected location.

Using the parameters above, the critical concentration of a given substance can be physically delivered to the site. The needles would subsequently pound, fill, or force the bioactive material into the dermis. This equates to a plethora of syringes perfectly delivering a given compound to the dermis. In this sense, the present invention offers a simultaneous injection of hundreds or even thousands of needles into the dermis to stimulate rejuvenation of the skin.

Note that the present invention is capable of delivering a given substance at different skin depths. This achieves depth selectivity for the present invention. In addition, this characteristic allows a bioactive material to reach a targeted cell in a specific area of the skin (e.g. at the stratum corneum, the bottom of the epidermis, the top of the dermis, or the middle of the dermis). It is the length (e.g. 0.15-2.5 mm), the angle (e.g. 12-25°), and the separation of the needles (e.g. 1.5-2.0 mm) that can control this depth penetration. The depth penetration flexibility benefit provided by the present invention allows for an enhanced specificity in terms of where the bioactive material is precisely delivered.

Figure 5A:
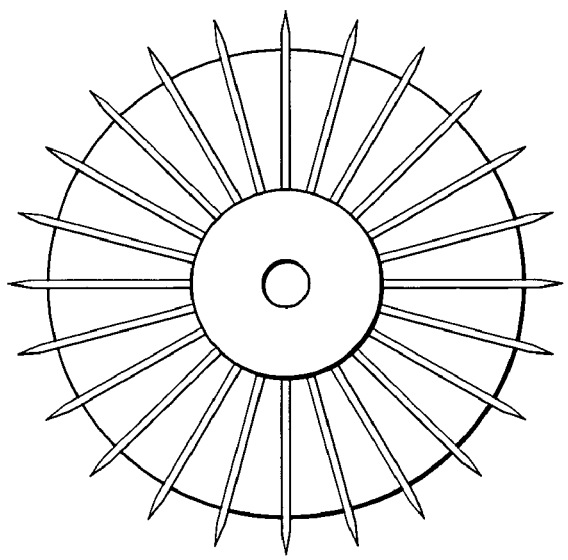
FIGS. 5A-5B are a set of simplified diagrams showing a top and a bottom perspective of the rolling device.
Figure 5B:
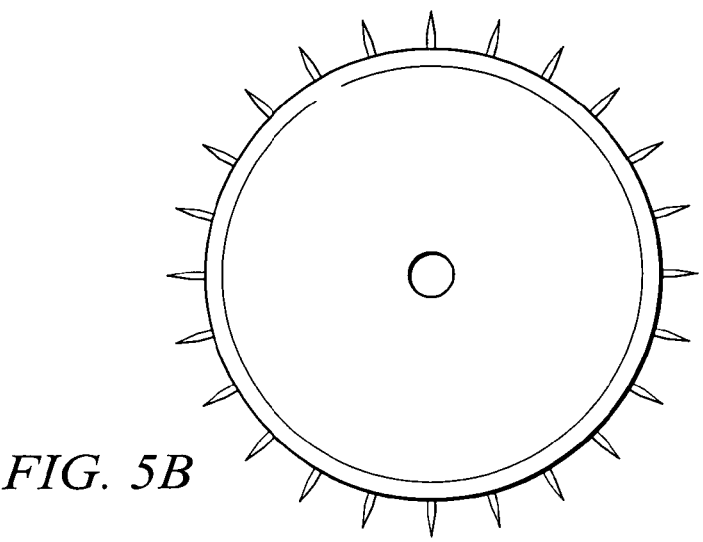

FIGS. 5A and 5B are a set of simplified diagrams showing a top and a bottom perspective of rolling device 10. The arrangement of FIGS. 5A and 5B has a scale of 4:1 in one example embodiment. The mechanism of the head provides suitable punctures at the stratum corneum and delivers the bioactive material on site. This operates to enhance collagen production by providing macromolecules (a peptide, a protein, a vitamin, a gene, a growth agent, etc.) to the dermis. As noted above, the rolling head operates to physically transport these important elements such that they reach the targeted areas where their benefits can be most realized.

Figure 6:
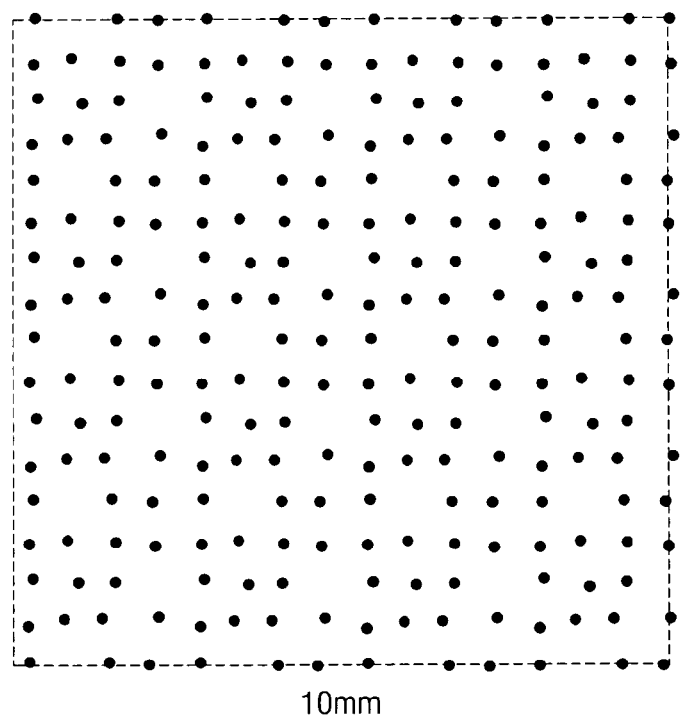
FIG. 6 is a simplified example diagram illustrating the needle pattern created by the rolling device in accordance with one embodiment of the present invention.
Figure 6:
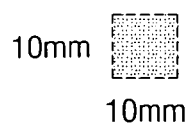

FIG. 6 is a simplified example diagram illustrating the needle pattern of rolling device 10 in accordance with one embodiment of the present invention. The example needle pattern of FIG. 6 has a scale of 10:1, as is illustrated. The example pattern of FIG. 6 reflects a needle length of 0.15 mm at an angle of 15 degrees. The distance from needle tip to needle tip is 2.6 mm in a rotating direction. The lateral distance is about 2.5 mm in this example. Theoretically, twelve roller movements per area will result in 236 pricks per square centimeter.

In order to penetrate the epidermal barrier for the infiltration of cosmetic substances, a pressure for rolling device 10 of about 300 grams is sufficient. The pressure on the skin may vary, but should generally not exceed 500 grams. In any case, the bioactive material should be applied on the skin before rolling starts. For optimal results, before the needling begins, the skin should be held tight. When reaching the targeted skin area, rolling device 10 should be lifted and slightly displaced before the return movement starts. This lifting and displacement ensures that the needles do not penetrate the previous prick channels. In any case, a constant back-and-forth movement, without lifting the roller, should be avoided.

It should also be recognized that the present invention can be implemented with a simple flat head design, as opposed to a rolling head as described in some of the preceding FIGURES. For example, a simple flat head could be employed (inclusive of a suitable number of needles as discussed above) and would achieve similar results as those outlined herein. In such an embodiment, the flat head would be lifted and then repositioned (repeatedly) in order to adequately pierce the surface of the skin. [Admittedly, the physics of a flat head design will be different than the general physics of a head capable of rolling. For example, the rolling embodiment leverages taut skin to achieve optimal punctures (via suitable hand pressure), whereas it would be difficult for the flat embodiment to reproduce a similar set of optimal holes.] Any suitable substance could be provided on the needles, which are included on the flat head. Such an embodiment is clearly within the scope of the broad teachings of the present invention. It should further be noted that the present invention is designed such that heads can readily be substituted for one another. This may result in certain needle lengths penetrating to one depth, whereby the head may be substituted for another head that produces a different depth. Such an operation could provide for the delivery of a substance or multiple substances at a specific region(s) of the skin (e.g. the dermis, the epidermis, etc.).

Alternative applications of the present invention may include vaccine delivery systems that rely on a precise delivery of the vaccine to achieve optimal results. Many vaccine candidates are highly purified, often times monomeric antigens, and as a result, are not very immunogenic. It is of extreme importance to have an antigen delivery system that will optimize the presentation of antigens to the human body. The skin is a major immunologic organ, with a dense network of potent antigen presenting cells, mainly Langerhans cells (LCs), covering approximately 15% of the epidermal/dermal boundary. Foreign antigens that penetrate the skin's primary barrier (i.e. stratum corneum) are taken up by the LCs, which migrate to draining lymph nodes, resulting in activation of antigen-specific immunity.

Another application of the present invention is gene therapy. The skin is an attractive organ for the development of therapeutic and prophylactic genetic medicines. The tissue is easily accessed, is well characterized at both cellular and molecular levels, has a significant regenerative capacity, and is easily monitored directly or via biopsy. The ability to target genes directly to the skin provides a strategy for the localized treatment of heritable skin diseases, such as epidermolysis bullosa simplex, various types of malignancies or infectious diseases.

Yet another application of the present invention involves drug therapy. The present invention may be used to deliver any drug (e.g. a local or a topical anesthetic drug) to any region of the skin (e.g. to the surface of the skin, to the dermis, the epidermis, etc.). Such drugs may include fentanyl citrate (Fentanyl), insulin, growth hormone, and local anesthetics such as bupivacaine (Marcaine, Bupivac), lidocaine (Xylocaine), mepivacaine (Carbocain), hydroquinone, etc. Other drug candidates could include procaine (Novocain), tetracaine (Pontocaine), and topical anesthetics, such as benzocaine, dibucaine, pramoxine, and butamben. Retinoic-acid is also a candidate for such operations. Still other drug candidates could include any substance whose potency or efficacy is enhanced by penetrating the surface of the skin.

Consider another example that involves tattoo removal. In general, lasers are used for such a procedure and the treatment can be quite painful for the patient. A terrific way of numbing the tattoo site of the patient is by using the present invention. In other contexts (for example, those involving pigmentation issues), hydroquinone could be delivered to the epidermal/dermal junction without incurring excessive toxicity. Thus, any number of applications could benefit from the teachings of the present invention.

Scar treatment is another area that could benefit greatly from the present invention. In addition to wound and surgical scars, there are acne scars and burn scars (contractures) that could easily leverage the present invention. Scars are often considered trivial, but they can be disfiguring, aesthetically unpleasant, and cause itching, tenderness, pain, etc. Rolling device 10 can readily be used on almost any kind of scar tissue in order to improve the appearance of the multi-scared skin of a patient. As mentioned above, acne scars could also be addressed by rolling device 10. The various types of acne scars can be broadly categorized into two main groups: 1) acne scars involving tissue loss; and 2) acne scars involving tissue excess. Both types of acne scars can be successfully treated with rolling device 10.

Other typical scars that can be treated with rolling device 10 can include: facelift scars, hair transplantation scars, surgical abdominal scars (appendectomy, Cesarean section, abdominoplasty, etc.), thoracic scars, breast operation scars (e.g. breast augmentation, breast reduction, breast), reconstruction scars, post liposuction scars, orthopedic scars (knee, femoral, arm, vertebral scars, etc.), etc.

Note that the example embodiments described above can be replaced with a number of potential alternatives where appropriate. The processes and configurations discussed herein only offer some of the numerous potential applications of rolling device 10. The elements and operations listed in FIGS. 1-6 may be achieved with use of rolling device 10 in any number of contexts and applications. Accordingly, delivery components, suitable physician-assistance, adequate support personnel, and any other appropriate objects may cooperate with rolling device 10 to effectuate the tasks and operations of the elements and activities associated with rejuvenating the skin. Accordingly, FIGS. 1-6 only offer one example of a suitable platform from which the present invention may be implemented.

Although the present invention has been described in detail with reference to particular embodiments in FIGS. 1-6, it should be understood that various other changes, substitutions, and alterations may be made hereto without departing from the sphere and scope of the present invention. For example, although the preceding FIGURES have referenced a number of design specifications that may be included in a given rolling device, any suitable characteristics or relevant parameters may be readily substituted for such elements and, similarly, benefit from the teachings of the present invention. Additionally it should be noted that although the example embodiments have described particular agents that may be used in cooperation with rolling device 10, any suitable substance could be used to achieve the operations of the present skin rejuvenation system of the present invention.

Numerous other changes, substitutions, variations, alterations, and modifications may be ascertained to one skilled in the art and it is intended that the present invention encompass all such changes, substitutions, variations, alterations, and modifications as falling within the spirit and scope of the appended claims.

What is claimed is:

1. An apparatus for delivering a bioactive material to a subterranean layer of a skin architecture, comprising:
    a head including one or more needles that are operable to penetrate a stratum corneum of a skin, wherein a bioactive material is disposed on one or more of the needles, whereby movement of the head operates to pick up the bioactive material and to deliver a portion of the bioactive material to a selected location, the selected location being a dermis, or an epidermis, or both the dermis and the epidermis, wherein rolling the apparatus over an area of the skin fifteen times will result in at least 200 pricks/centimeter squared, and wherein the bioactive material is formulated to cause collagen proliferation.

2. The apparatus of claim 1, wherein the bioactive material is a macromolecule substance that is part of a group of substances, the group consisting of:
   a) a protein;
   b) a vitamin;
   c) a gene;
   d) a growth agent;
   e) a peptide; and
   f) a drug.

3. The apparatus of claim 1, wherein the needles create an injury that triggers collagen production from one or more fibroblasts in the skin.

4. The apparatus of claim 1, wherein the needles are operable to create holes in the stratum corneum, the holes being in a range of 0.02 mm to 0.18 mm in diameter.

5. The apparatus of claim 1, wherein the needles are positioned at an angle having a range between 12° and 25° when compared to the head, which is used as a reference point for angle determination.

6. The apparatus of claim 1, wherein the needles are provided in an arrangement that includes between 6 and 14 needle rows.

7. The apparatus of claim 1, wherein the needles are of a length of about 0.15 mm to 2.5 mm.

8. The apparatus of claim 1 further comprising:
   a fork element coupled to the head and operable to provide a holding mechanism for an end user of the apparatus.

9. The apparatus of claim 1, wherein the head has a width between 5 mm and 30 mm.

10. The apparatus of claim 1, wherein the bioactive material is delivered at the stratum corneum of the skin, to the bottom of the epidermis, to the top of the dermis, or to the middle of the dermis, and wherein a depth of delivery of the bioactive material is determined by a length, an angle, and a needle separation associated with the needles, and wherein the separation of the needles is in a range of 1.5-2.0 mm.

11. The apparatus of claim 1, wherein the head is a selected one of a roller head and a flat head.

12. The apparatus of claim 1, wherein the delivery of the bioactive material comprises a physical transport of the bioactive material.

13. A method, comprising:
   providing a head with one or more needles that are operable to penetrate a stratum corneum of a skin; and
   manufacturing the head to allow for positioning of a bioactive material on one or more of the needles, whereby movement of the head operates to pick up the bioactive material and to deliver a portion of the bioactive material to a selected location, the selected location being a dermis, or an epidermis, or both the dermis and the epidermis, wherein rolling the head over an area of the skin fifteen times will result in at least 200 pricks/centimeter squared, and wherein the bioactive material is formulated to cause collagen proliferation.

14. The method of claim 13, wherein the bioactive material is a macromolecule substance that is part of a group of substances, the group consisting of:
   a) a protein;
   b) a vitamin;
   c) a gene;
   d) a growth agent;
   e) a peptide; and
   f) a drug.

15. The method of claim 13, wherein the needles create an injury that triggers collagen production from one or more fibroblasts in the skin.

16. The method of claim 13, further comprising:
   positioning the needles on the head in order to create holes in the stratum corneum, the holes being in a range of 0.02 mm to 0.18 mm in diameter.

17. The method of claim 13, further comprising:
   positioning the needles at an angle having a range between 12° and 25° when compared to the head, which is used as a reference point for angle determination.

18. The method of claim 13, further comprising:
   positioning the needles in an arrangement that includes between 6 and 14 needle rows.

19. The method of claim 13, wherein the head is designed to be used in a selected application, the application being part of a group of applications, the group consisting of:
   a) percutaneous collagen induction therapy;
   b) vaccine delivery;
   c) gene therapy;
   d) scarring applications; and
   e) drug applications.

20. The method of claim 13, further comprising:
   providing the head with a fork element coupled to the head and operable to provide a holding mechanism for an end user of the apparatus.

21. The method of claim 13, further comprising:
   packaging the head along with the bioactive material such that the head and the bioactive material can cooperate and be used together.

22. The method of claim 13, further comprising:
   providing a stand that may be used to support or to stabilize the device.

23. The method of claim 13, wherein the needles are of a length of about 0.15 mm to 2.5 mm and the head has a width between 5 mm and 30 mm.

24. The method of claim 13, wherein a separation of the needles is in a range of 1.5-2.0 mm.

25. The method of claim 13, wherein a depth of delivery of the bioactive material is determined by a length, an angle, and a needle separation associated with the needles.

* * * * *